US 8,187,524 B2

(12) United States Patent
Yano

(10) Patent No.: US 8,187,524 B2
(45) Date of Patent: May 29, 2012

(54) APPARATUS AND METHOD FOR MANUFACTURING ABSORBENT BODY

(75) Inventor: Takanori Yano, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 0 days.

(21) Appl. No.: 13/054,175

(22) PCT Filed: Jul. 29, 2009

(86) PCT No.: PCT/JP2009/063473
§ 371 (c)(1),
(2), (4) Date: Mar. 28, 2011

(87) PCT Pub. No.: WO2010/013737
PCT Pub. Date: Feb. 4, 2010

(65) Prior Publication Data
US 2011/0180976 A1 Jul. 28, 2011

(30) Foreign Application Priority Data
Jul. 31, 2008 (JP) ................................ 2008-198348

(51) Int. Cl.
A61F 13/15 (2006.01)
D04H 1/72 (2012.01)
(52) U.S. Cl. ........ 264/517; 264/518; 425/80.1; 425/83.1
(58) Field of Classification Search .................. None
See application file for complete search history.

(56) References Cited

U.S. PATENT DOCUMENTS

| 4,264,290 A * | 4/1981 | Dunkerly et al. ............ 425/83.1 |
| 4,276,248 A * | 6/1981 | Widnell ........................ 264/121 |
| 6,877,970 B2 | 4/2005 | Tange et al. |
| 2001/0054783 A1 | 12/2001 | Kobayashi et al. |

FOREIGN PATENT DOCUMENTS

| JP | 54-101982 | 8/1979 |
| JP | 01-298219 | 12/1989 |
| JP | 2001-288670 | 10/2001 |
| JP | 2002-317373 | 10/2002 |
| JP | 2006-122138 | 5/2006 |
| JP | 2006-132009 | 5/2006 |

OTHER PUBLICATIONS

International Search Report from corresponding PCT application No. PCT/JP2009/063473 dated Oct. 27, 2009, 4 pgs.

* cited by examiner

Primary Examiner — Mary F Theisen
(74) Attorney, Agent, or Firm — Brinks Hofer Gilson & Lione

(57) ABSTRACT

An apparatus for manufacturing an absorbent body, having a recessed form die formed on a predetermined face of a predetermined member, moving in one direction along a moving path along the predetermined face; a duct disposed in a predetermined position in the moving path, discharging a gas including fluid absorbent fibers from an opening section toward the predetermined face, an absorbent body being formed by suction of the gas through intake holes at a bottom section of the form die to stack into the form die the fluid absorbent fibers included in the gas when the form die passes by the position of the duct. A gap is formed between the predetermined face and the opening section of the duct. A gas pressure inside the duct is lower than a gas pressure outside the duct by suction of the gas from the bottom section of the form die. A first wall is outside the duct. The first wall is spaced from a wall of the duct by a first spacing and spaced from the predetermined face by a second spacing. An outside gas flow along a direction intersecting with the predetermined face and an outside gas flow along the predetermined face is made to reach the gap by the first wall.

11 Claims, 6 Drawing Sheets

APPARATUS AND METHOD FOR MANUFACTURING ABSORBENT BODY

RELATED APPLICATION

The present application is a 35 U.S.C. §371 national stage filing of International Patent Application No. PCT/JP2009/063473, filed Jul. 29, 2009, to which priority is claimed under 35 U.S.C. §120 and through which priority is claimed under 35 U.S.C. §119 to Japanese Priority Patent Application No. 2008-198348, filed Jul. 31, 2008.

TECHNICAL FIELD

The present invention relates to an apparatus and a method for manufacturing an absorbent body of an absorbent article such as a disposable diaper.

BACKGROUND ART

As examples of an absorbent article that absorbs fluid, disposable diapers, sanitary napkins, and the like are used. These absorbent articles include an absorbent body 1 that is produced by forming pulp fibers into a predetermined shape.

This absorbent body 1 is formed by a fiber stacking apparatus 10a in a production line. FIG. 1 is a side view of the fiber stacking apparatus 10a partially showing a longitudinal section thereof. The fiber stacking apparatus 10a includes as the main body, a rotating drum 20 that rotates in one direction Dc. There are recessed shaped form dies 21 provided on the outer circumferential surface 20a of the rotating drum 20, which are configured to allow air suction from the bottom thereof. Further, there is also a distribution opening 31a of a duct 31 provided so as to oppose the outer circumferential surface 20a of the rotating drum 20. And from the distribution opening 31a, mixed air 3 discharged from the distribution opening 31a having pulp fiber 2 contained therein is discharged toward the outer circumferential surface 20a.

Thus, when a form die 21 passes by the position of the distribution opening 31a as the rotating drum 20 rotates, mixed air 3 discharged from the distribution opening 31a is drawn in from the bottom of this form die 21. And along with this, owing to the suction force generated inside the form die 21, the pulp fibers 2 in the mixed air 3 stack in the form die 21 to form an absorbent body 1 (see patent document 1).

[Patent Document 1]
Japanese Patent Application Laid-open Publication No. 2006-132009

DISCLOSURE OF INVENTION

Problem to be Solved by the Invention

Here, in order to stack pulp fibers 2 uniformly in the form die 21, it is essential to restrain the turbulent flow inside the duct 31. As a result of studies made in this regard by the applicants by fluid analysis and the like, it was found that intrusion of outside air through the gap G between the outer circumferential surface 20a of the rotating drum 20 and the distribution opening 31a of the duct 31 has a large influence on the generation of the turbulent flow.

In other words, as mentioned above, for the purpose of stacking the absorbent body 1, air is drawn in from the bottom of the form die 21 of the rotating drum 20. This drawing of air allows the air pressure within the duct 31 to be maintained lower (hereinafter also referred to as "negative pressure") than that outside the duct 31. Therefore, outside air intrudes into the duct 31 through the gap G between the outer circumferential surface 20a of the rotating drum 20 and the distribution opening 31a of the duct 31. And this intruding of air causes a turbulent flow such as a vortex at for example a region proximate the gap G within the duct 31. And as a result, uniform stacking of the pulp fibers 2 is inhibited.

As a method of preventing this intrusion of outside air, there is, such as, inserting a brush shaped contact seal (not shown) in the gap G. However, since this contact seal slides against at least one of the outer circumferential surface 20a of the rotating drum 20 or the distribution opening 31a of the duct 31 and wears out, this results in need for maintenance work such as periodical replacement.

When a contact seal is used particularly for the gap G at the downstream side in the circumferential direction Dc, of the gaps G between the outer circumferential surface 20a of the rotating drum 20 and the distribution opening 31a of the duct 31, this contact seal would contact the absorbent body 1 stacked in the form die 21 to flip the absorbent body 1. Therefore, as a contact seal, there is a case where a roll seal that rolls while abutting against the outer circumferential surface 20a of the rotating drum 20 is used. However, the result is that this cannot be used either since a turbulent flow is caused at a region proximate the gap G within the duct 31 by the rotation of this roll seal.

The present invention was made in light of conventional problems as those described above, and it is an object thereof to provide an apparatus and a method for manufacturing an absorbent body, which is enabled to constrain the intrusion of outside air into the duct without providing, as much as possible, a contact seal.

Means for Solving the Problem

In order to solve the problems as described above, a main aspect of the present invention is an apparatus for manufacturing an absorbent body including a form die that is formed in a recessed shape on a predetermined surface of a predetermined member and that moves in one direction along a moving path along the predetermined surface; and a duct that is positioned at a predetermined position on the moving path and that discharges gas containing fluid absorbent fiber from an opening toward the predetermined surface; wherein an absorbent body is formed by suction of the gas through an intake hole at a bottom of the form die to stack into the form die fluid absorbent fiber contained in the gas when the form die passes by the position of the duct, the apparatus further having a gap formed between the predetermined surface and an opening of the duct, a gas pressure inside the duct that is lower than a gas pressure outside the duct by suction of the gas from the bottom of the form die, a first wall outside the duct, the first wall spaced from a wall of the duct by a first spacing and spaced from the predetermined surface by a second spacing, and an outside gas flow along a direction intersecting with the predetermined surface and an outside gas flow along the predetermined surface made to reach the gap by the first wall.

Another main aspect of the present invention is a method for manufacturing an absorbent body using a form die that is formed in a recessed shape on a predetermined surface of a predetermined member and that moves in one direction along a moving path along the predetermined surface; and using a duct that is positioned at a predetermined position on the moving path and that discharges gas containing fluid absorbent fiber from an opening toward the predetermined surface;

wherein the method for manufacturing an absorbent body is for forming an absorbent body by suction of the gas through an intake hole at a bottom of the form die to stack into the form die fluid absorbent fiber contained in the gas when the form die passes by the position of the duct, the method further includes forming a gap between the predetermined surface and an opening of the duct, keeping a gas pressure inside the duct lower than a gas pressure outside the duct by suction of the gas from the bottom of the form die, spacing a first wall, outside the duct, from a wall of the duct by a first spacing and from the predetermined surface by a second spacing, and making an outside gas flow along a direction intersecting with the predetermined surface and an outside gas flow along the predetermined surface reach the gap by the first wall.

Other features of the present invention will become apparent from the description of the present specification with reference to the accompanying drawings.

Effects of the Invention

According to the present invention, intrusion of outside air into the duct can be restrained without providing, as much as possible, a contact seal.

BRIEF DESCRIPTION OF DRAWINGS

FIG. 1 is a side view, partially a longitudinal section, of a fiber stacking apparatus 10a.

BEST MODE FOR CARRYING OUT THE INVENTION

Figure 1:
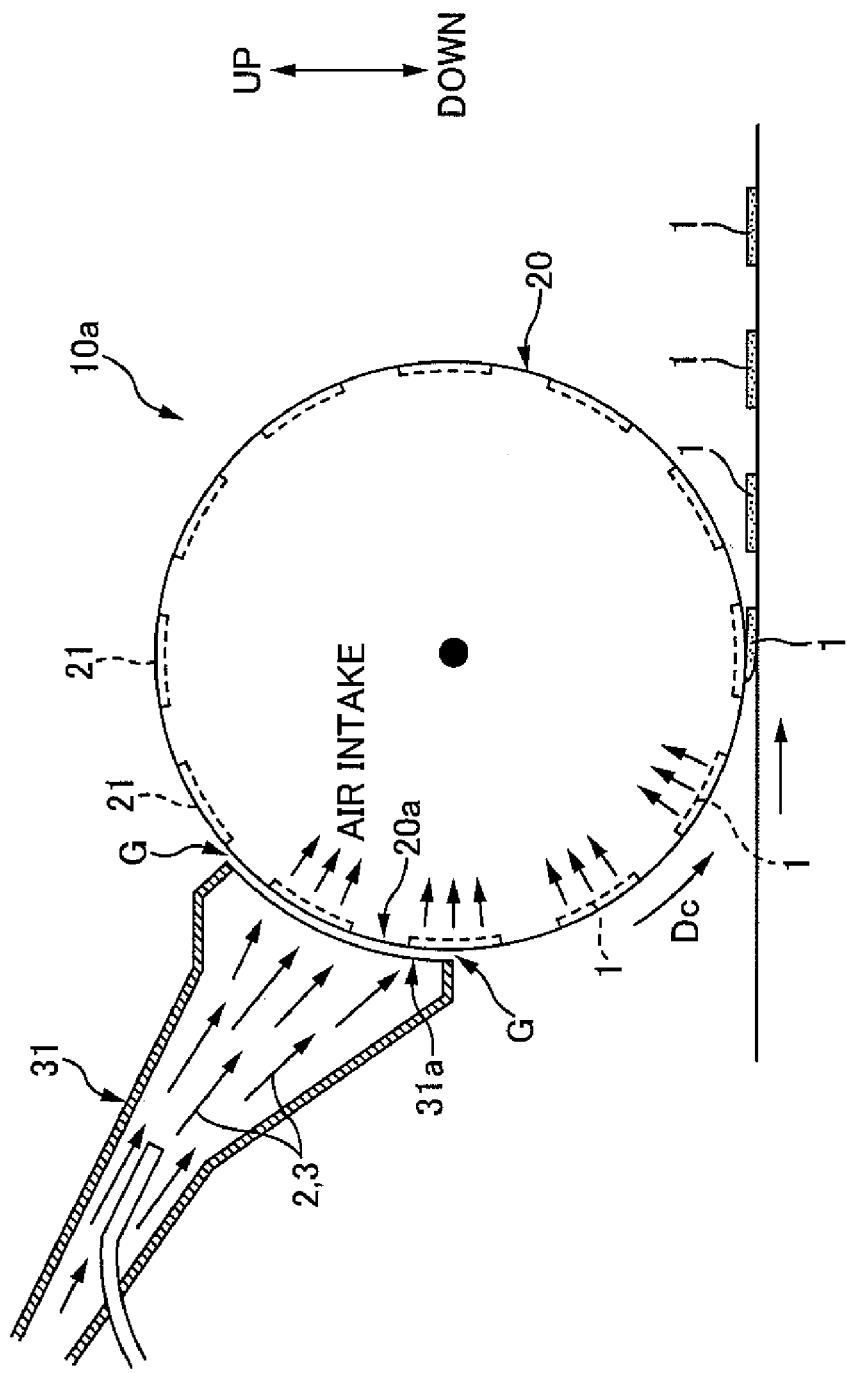

At least the following matters will be made clear from the description of the present specification with reference to the accompanying drawings.

In order to solve the above described problems, a main aspect of the present invention is an apparatus for manufacturing an absorbent body including a form die that is formed in a recessed shape on a predetermined surface of a predetermined member and that moves in one direction along a moving path along the predetermined surface; and a duct that is positioned at a predetermined position on the moving path and that discharges gas containing fluid absorbent fiber from an opening toward the predetermined surface; wherein an absorbent body is formed by suction of the gas through an intake hole at a bottom of the form die to stack into the form die fluid absorbent fiber contained in the gas when the form die passes by the position of the duct, the apparatus further having a gap formed between the predetermined surface and an opening of the duct, a gas pressure inside the duct that is lower than a gas pressure outside the duct by suction of the gas from the bottom of the form die, a first wall outside the duct, the first wall spaced from a wall of the duct by a first spacing and spaced from the predetermined surface by a second spacing, and an outside gas flow along a direction intersecting with the predetermined surface and an outside gas flow along the predetermined surface made to reach the gap by the first wall.

According to such an apparatus for manufacturing an absorbent body, by positioning a first wall, outside air, besides the outside air that flows along the predetermined surface, is allowed to flow along a direction that intersects the predetermined surface to reach the gap. In other words, the flow of outside air that is to reach the gap is certainly divided into two flows. And the latter of the two flows is the one that flows in a direction that intersects with the specific surface so that it is forced to turn to change its direction toward the gap immediately before reaching the gap, which leads to a dynamic pressure drop. Compared with the case where the first wall is not provided, energy of outside air decreases by an amount of at least the dynamic pressure lost. This results in restraining the intrusion of outside air through the gap.

Further, it is considered that the outside air flow along the direction intersecting the specific surface interferes with the outside air flow along the specific surface. So that when comparing with the case where the first wall is not provided, the intensity of the outside air flow along the specific surface is restrained and as a result the outside air intruding through the gap is restrained.

Additionally, since the first wall does not contact the specific surface, the trouble of component replacement due to wear by sliding can be relieved.

Another main aspect of the present invention is an apparatus for manufacturing an absorbent body in which the first wall is provided to at least either a wall of the duct located at an upstream side of the moving path or a wall of the duct located at a downstream side of the moving path.

According to such an apparatus for manufacturing an absorbent body, intrusion of outside air through at least the upstream side gap or the downstream side gap, of the gaps, in the moving path can be restrained.

Another main aspect of the present invention is an apparatus for manufacturing an absorbent body in which a pair of side walls are provided, the side walls extending between the wall of the duct and the first wall to close the first spacing from the sides.

According to such an apparatus for manufacturing an absorbent body, owing to the provision of a pair of side walls closing the first spacing form the sides, intrusion of outside air through a gap is restrained.

Another main aspect of the present invention is an apparatus for manufacturing an absorbent body in which a first chamber is partitioned adjacent to the gap with the first wall and the wall of the duct, the first chamber being in communication with the inside of the duct via the gap, and gas pressure inside the first chamber is set lower than a gas pressure outside the duct and higher than a gas pressure inside the duct.

According to such an apparatus for manufacturing an absorbent body, the first chamber functions as a pressure moderating portion that restrains a sudden change of pressure from a high air pressure outside the duct to a low air pressure inside the duct. Therewith, the flow rate of outside air intruding into the duct through the gap can be reduced. And as a result, the intrusion of outside air into the duct can be restrained.

Further, since the flow rate of the outside air flowing along the moving path (specific surface) is reduced, peeling of the fluid absorbent fiber from the absorbent body stacked in the form die can be avoided so that uniform stacking can be achieved.

Another main aspect of the present invention is an apparatus for manufacturing an absorbent body in which at least one or more opposing walls are spaced from an adjacent wall, including the first wall, in a direction along the moving path at positions, along the moving path, that are farther away from the wall of the duct than the first wall, the walls being spaced from the predetermined surface, gas pressure inside each of the chambers partitioned by adjacent walls along the moving path becomes closer to a gas pressure outside the duct as each of the chambers, including the first chamber, are farther away from the wall of the duct.

According to such an apparatus for manufacturing an absorbent body, a plurality of chambers, including the first chamber, are sectionally formed along the moving path in a way such that the farther away from the duct the chamber is, the closer to the air pressure outside the duct the air pressure therein becomes. Thus the above mentioned effect as a pressure moderating section increases accordingly as the number of chambers increases, that is, the pressure gradient across the duct inside and the duct outside can be made very moderate. As a result, the flow rate of the outside air intruding into the duct can be reduced.

Since the flow rate of the outside air flowing along the moving path (specific surface) is reduced, peeling of the fluid absorbent fiber from the absorbent body stacked in the form die can be avoided so that uniform stacking can be achieved.

Further, as the wall is placed apart from the specific surface with a spacing therebetween, the specific surface is in a non-contact state. Thus the trouble of component replacement due to wear by sliding can be relieved.

Another main aspect of the present invention is an apparatus for manufacturing an absorbent body in which each of the chambers have a pair of side walls that extend between the adjacent walls in the direction along the moving path to close the sides of the chamber, and a ceiling that extend between the adjacent walls in the direction along the moving path and that is positioned to oppose the predetermined surface, and the ceiling has a plurality of penetration holes formed thereto.

According to such an apparatus for manufacturing an absorbent body, the air pressure in the chamber can be adjusted such as by setting the number or the diameter of the plurality of penetration holes so that adjustment of air pressure is made easier.

Because the penetration holes are formed at the ceiling, the outside air flowing into the chamber through the penetration holes can be reliably straightened to flow in a direction that intersects with the moving path (specific surface). Therewith, a dynamic pressure drop can be reliably caused when changing the direction toward the gap and as a result, the intrusion of outside air through the gap can be reliably restrained.

Another main aspect of the present invention is an apparatus for manufacturing an absorbent body in which a ratio of an area of the plurality of penetration holes to an area of the ceiling becomes larger as a chamber of the plurality of chambers, including the first chamber, is farther away from the wall of the duct.

According to such an apparatus for manufacturing an absorbent body, easy and reliable pressure adjustment can be performed such that the farther away from the duct the chamber is, the closer to the air pressure outside the duct the air pressure therein becomes.

Another main aspect of the present invention is an apparatus for manufacturing an absorbent body in which a size of a spacing between the walls, except the wall of the duct, and the predetermined surface is smaller than a spacing between the wall of the duct and the predetermined surface and larger than zero.

According to such an apparatus for manufacturing an absorbent body, since the spacing between the wall and the specific surface is smaller than that between the wall of the duct and the specific surface, intrusion of outside air along the moving path (specific surface) into the duct through the gap can be effectively restrained.

Another main aspect of the present invention is an apparatus for manufacturing an absorbent body in which a suction of gas from the bottom of the form die is also performed at the first spacing between the first wall and the wall of the duct.

According to such an apparatus for manufacturing an absorbent body, an airflow that flows in the first spacing along the direction that intersects with the specific surface can be reliably formed so that intrusion of outside air through the gap between the wall of the duct and the specific surface can be effectively restrained.

Another main aspect of the present invention is an apparatus for manufacturing an absorbent body in which the predetermined member is a rotating drum that continuously rotates in one direction along a circumferential direction, the form die is formed in a recessed shape on an outer circumferential surface, as the predetermined surface, of the rotating drum, and the form die is moved along the path in the circumferential direction as the moving path along with a rotation of the rotating drum in the circumferential direction, and the opening of the duct is provided to oppose the outer circumferential surface of the rotating drum at a predetermined location in the circumferential direction.

Another main aspect of the present invention is a method for manufacturing an absorbent body using a form die that is formed in a recessed shape on a predetermined surface of a predetermined member and that moves in one direction along a moving path on the predetermined surface; and using a duct that is positioned at a predetermined position on the moving path and that discharges gas containing fluid absorbent fiber from an opening toward the predetermined surface; wherein the method for manufacturing an absorbent body is for forming an absorbent article by suction of the gas through an intake hole at a bottom of the form die to stack into the form die fluid absorbent fiber contained in the gas when the form die passes by the position of the duct, the method further includes forming a gap between the predetermined surface and an opening of the duct, keeping a gas pressure inside the duct lower than a gas pressure outside the duct by suction of the gas from the bottom of the form die, spacing a first wall, outside the duct, from a wall of the duct by a first spacing and from the predetermined surface by a second spacing, and making an outside gas flow along a direction intersecting with the predetermined surface and an outside gas flow along the predetermined surface reach the gap by the first wall.

According to such a method for manufacturing an absorbent body, by positioning a first wall, outside air, besides the outside air that flows along the predetermined surface, is allowed to flow along a direction that intersects the predetermined surface to reach the gap. In other words, the flow of outside air that is to reach the gap is certainly divided into two flows. And the latter of the two flows is the one that flows in a direction that intersects the specific surface so that it is forced to turn to change its direction toward the gap immediately before reaching the gap, which leads to a dynamic pressure drop. Compared to the case where the first wall is not provided, energy of outside air decreases by an amount of at least the dynamic pressure lost. This results in restraining the intrusion of outside air through the gap.

Further, it is considered that the outside air flow along the direction intersecting the specific surface interferes with the outside air flowing along the specific surface. So that compared to the case where the first wall is not provided, the strength of the outside air flow along the specific surface is restrained and as a result the outside air intruding through the gap is restrained.

Additionally, since the first wall does not contact the specific surface, the trouble of replacing the component due to wear by sliding can be relieved.

The First Embodiment

Figure 2:
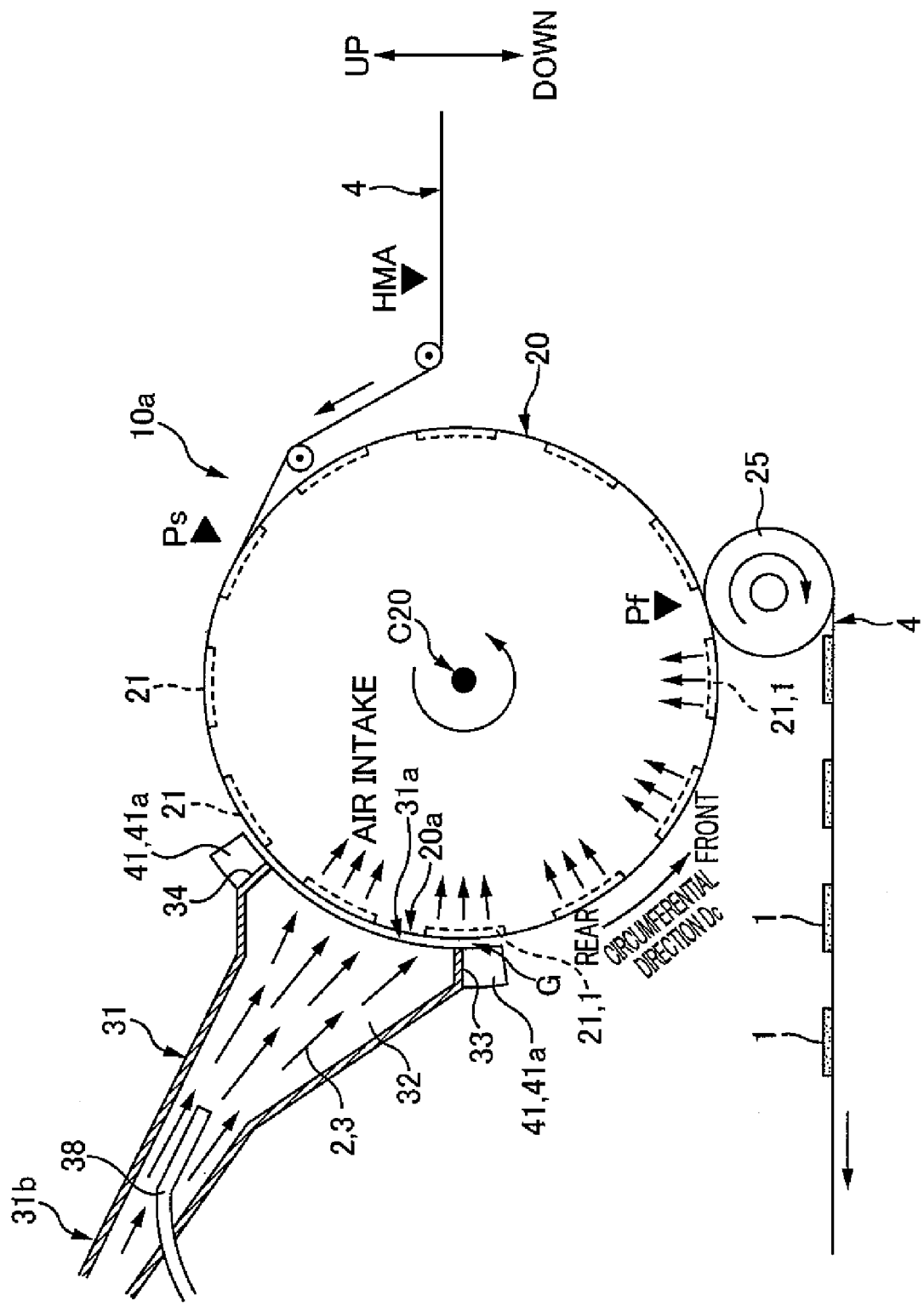
FIG. 2 is an explanatory diagram of an apparatus 10 for manufacturing an absorbent body 1 according to the first embodiment.

FIG. 2 is a side view of an apparatus 10 for manufacturing an absorbent body 1 according to the first embodiment showing only the duct 31 of the manufacturing apparatus 10 in a longitudinal sectional view.

The apparatus 10 for manufacturing the absorbent body 1 according to the first embodiment is a so-called fiber stacking apparatus that forms an absorbent body 1 by stacking pulp fibers 2 as fluid absorbent fiber into layers. As its main components, the manufacturing apparatus 10 is equipped with a rotating drum 20 (corresponding to specific member) that continuously rotates in one direction (anti-clockwise direction, for example) of the circumferential direction Dc with a horizontal axis C20 as the rotating center, and a duct 31 that discharges pulp fibers 2 positioned at a predetermined location in the circumferential direction Dc of the rotating drum 20. Incidentally, in the following description, the circumferential direction Dc of the rotating drum 20 is simply referred to as "circumferential direction" or "front-rear direction" and the direction along the horizontal axis C20 of the rotating drum 20 (direction that penetrates the plane of FIG. 2) is also referred to as the "width direction" or the "horizontal direction."

The rotating drum 20 includes a cylindrical body, with a horizontal axis C20 at its center, as its main body. On the outer circumferential surface 20a (corresponding to specific surface) there are provided form dies 21 in recessed shapes corresponding to the shape of the absorbent body 1 to be formed at predetermined intervals in the circumferential direction Dc, and a multiple number of air intake holes (not shown) are formed on the bottom of each form die 21.

The duct 31, for example, is a tubular shaped member with a substantially rectangular section, which is disposed obliquely above the rotating drum 20. The duct 31 is mainly configured with a pair of side walls 32, 32 positioned on both sides in the width direction and a front wall 33 and a rear wall 34 positioned at the front and rear in the circumferential direction Dc. The distribution opening 31a (corresponding to opening), being an opening at the bottom end of the duct 31, covers a predetermined area of a part approximately obliquely above the outer circumferential surface 20a of the rotating drum 20. And from the upper end opening 31b of the duct 31, pulp fibers 2 that have been pulverized by a pulverizing device are provided along with air flow 3 so that mixed air 3 with pulp fibers 2 contained therein flow from upstream to downstream within the duct 31.

Thus, when the form die 21 passes the position of the distribution opening 31a by driving the rotating drum 20 to rotate, the mixed air 3 discharged form the distribution opening 31a is drawn in through the air intake holes of the form die 21. However, at this time, the passing by of the pulp fibers 2 is restrained so that pulp fibers 2 in the mixed air are stacked to form an absorbent body 1 at the bottom of the form die 21. Then after the form die 21 passes the position of the distribution opening 31a, when the outer circumferential surface 20a of the rotating drum 20 reaches a demolding position Pf where the outer circumferential surface 20a faces downward, absorbent body 1 is demolded from the form die 21 at position Pf. Thereafter, the absorbent body 1 is placed on a continuous sheet shaped member 4 such as nonwoven fabric or tissue paper to be transferred to a subsequent process.

Incidentally, in the case of the example shown in FIG. 2, position Ps where the above mentioned sheet shaped member 4 is supplied to the rotating drum 20, is set to a position upstream to the duct 31 in the circumferential direction Dc of the rotating drum 20. Therefore, at the feeding position Ps, the sheet shaped member 4 rolled around the outer circumferential surface 20a of the rotating drum 20 moves in the circumferential direction Dc along with the rotating movement of the rotating drum 20 almost without slipping with regard to the outer circumferential surface 20a. Here, an absorbent body 1 is stacked on a part of the sheet shaped member 4 that abuts against the form die 21 when the form die 21 passes by the position of the duct 31. Thereafter, in due course, when the form die 21 moves to a position on the downstream side of the position where the duct 31 is located, with the roller 25 placed at the same location therewith, the sheet shaped member 4 is separated from the outer circumferential surface 20a of the rotating drum 20 so that the absorbent body 1 is demolded from the form die 21 onto the sheet shaped member 4.

In the example shown in FIG. 2, in duct 31, there is a charge duct 38 positioned for charging superabsorbent polymer to the absorbent body 1 that is being stacked, however this charge duct 38 is not requisite.

By the way, the air pressure within duct 31 is maintained at negative pressure that is lower than the air pressure outside the duct 31 (for example, the air pressure within duct 31 is at negative pressure 100 Pa to 6 KPa lower than that outside the duct 31) by suction of air from the above described bottom of the form die 21. Thus outside air intrudes into the duct 31 through the gap G between the distribution opening 31a of duct 31 and the outer circumferential surface 20a of the rotating drum 20. So there is fear that this intruding of air would cause a turbulent flow such as a vortex inside the duct 31 to inhibit pulp fibers 2 from being uniformly stacked.

In this regard, brush shaped contact seals (not shown in FIG. 2 but shown in FIG. 3A with reference numeral 32a attached) are respectively fixed to the side walls 32, 32 on both sides of the width direction that configure the duct 31 to close the gap G. This brush restrains the intrusion of outside air by contacting in a slidable manner with the outer circumferential surface 20a of the rotating drum 20.

However, when this contact seal is used for the front wall 33 and the rear wall 34 of the duct 31, besides the above mentioned problem of component replacement due to wear by sliding, inconveniences such as those given hereafter arises. That is to say, with an objective to fix the absorbent body 1 by bonding, there is a case where the aforementioned sheet shaped member 4 is provided to the rotating drum 20 with hot-melt adhesive (HMA) coated thereto. In such a case, when the sheet shaped member 4 passes the position of the duct 31, the sheet shaped member 4, with the hot-melt adhesive, adheres to the contact seal of the front wall 33 and the rear wall 34 so that the sheet shaped member 4 fails to be transferred in a stable manner.

So, to the front wall 33 and the rear wall 34 of the duct 31, outside air intrusion inhibiting members 41, 41 that can restrain the intrusion of outside air into the duct 31 are respectively applied in a non-contact state to the outer circumferential surface 20a of the rotating drum 20. By the way, the basic structure of both of the outside air intrusion inhibiting members 41, 41 of the front wall 33 (corresponding to the wall located at the downstream side) and the rear wall 34 (corresponding to the wall located at the upstream side) are substantially the same so that in the following description, explanation of the outside air intrusion inhibiting member 41 for the front wall 33, that is, the outside air intrusion inhibiting member 41 positioned on the downstream side of the duct 31 with respect to the circumferential direction Dc of the rotating drum 20, is given as example.

Figure 3A:
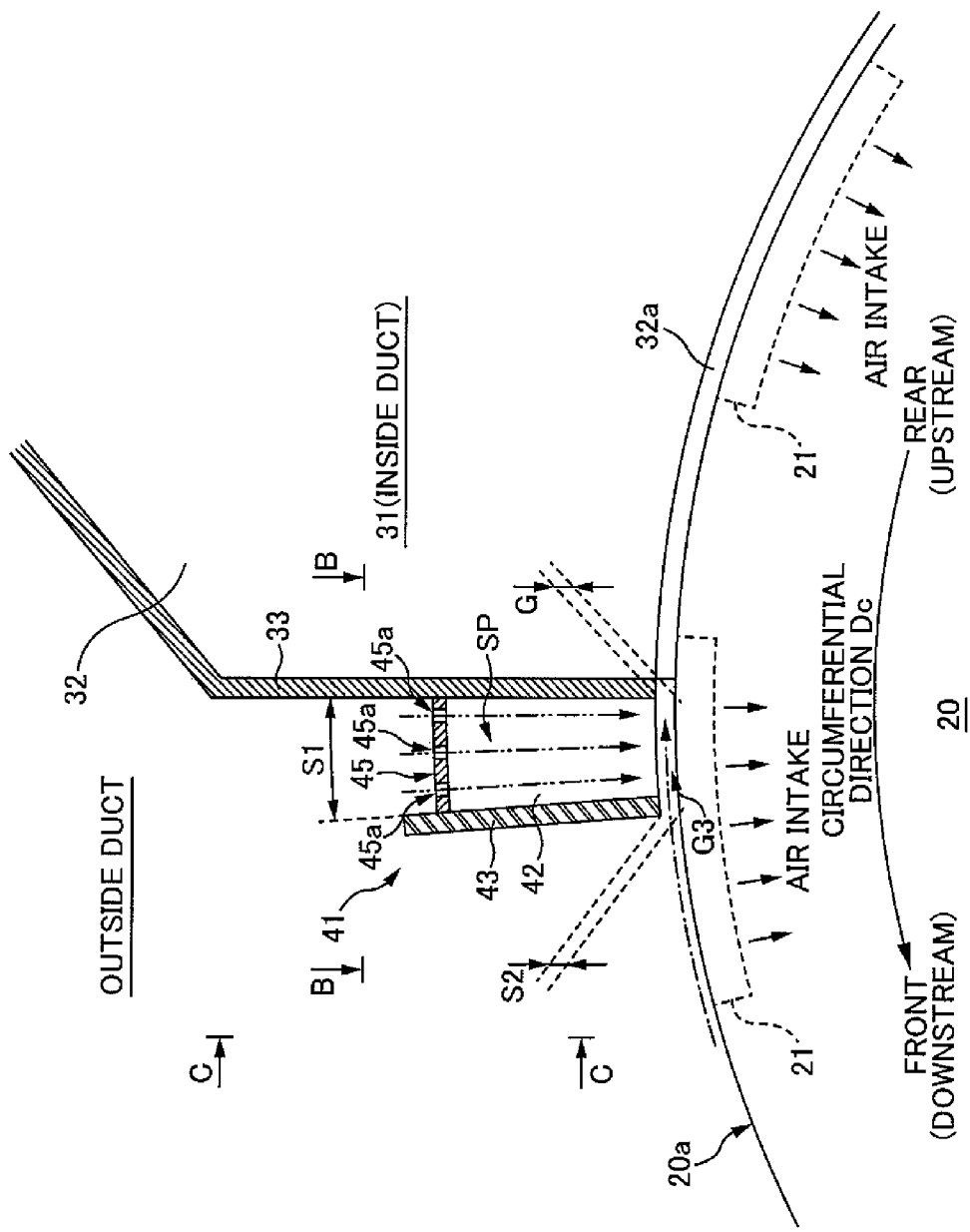
FIG. 3A is a longitudinal sectional view of the outside air intrusion inhibiting member 41.
Figure 3B:
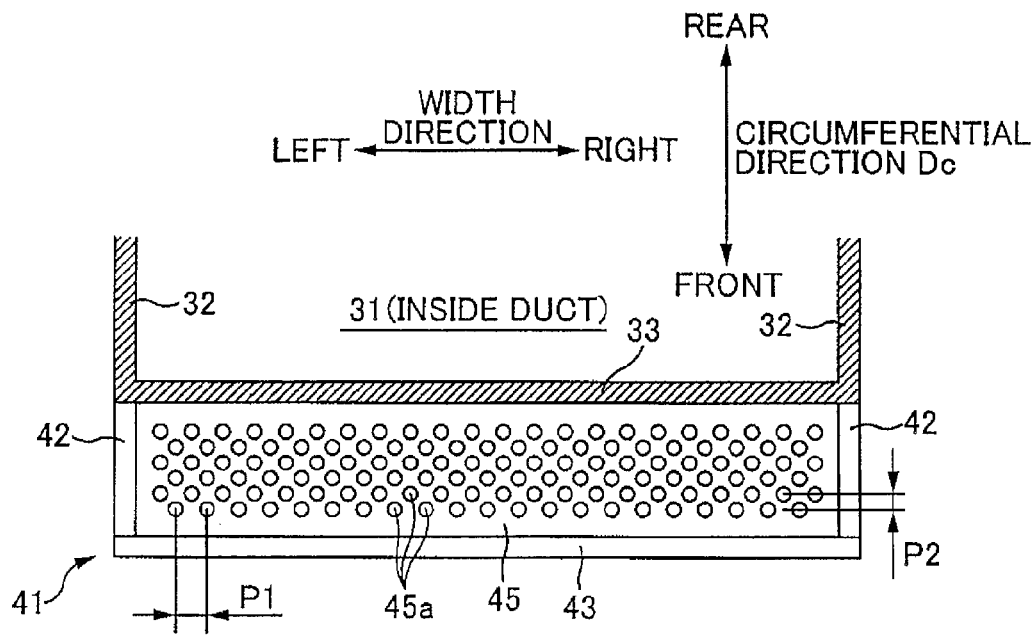
FIG. 3B is a view seen along line B-B in FIG. 3A.
Figure 3C:
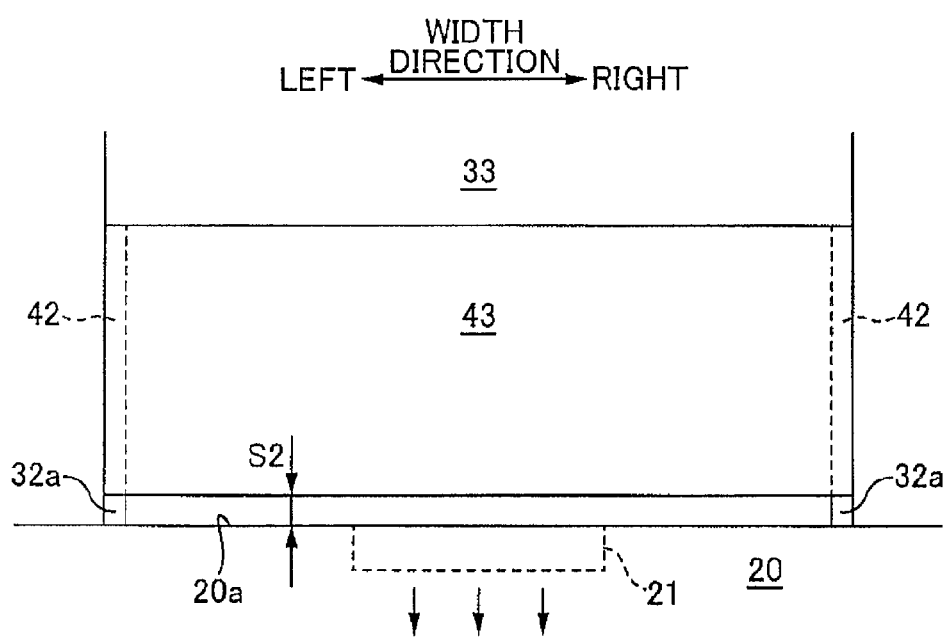
FIG. 3C is a view seen along line C-C in FIG. 3A.
Figure 4:
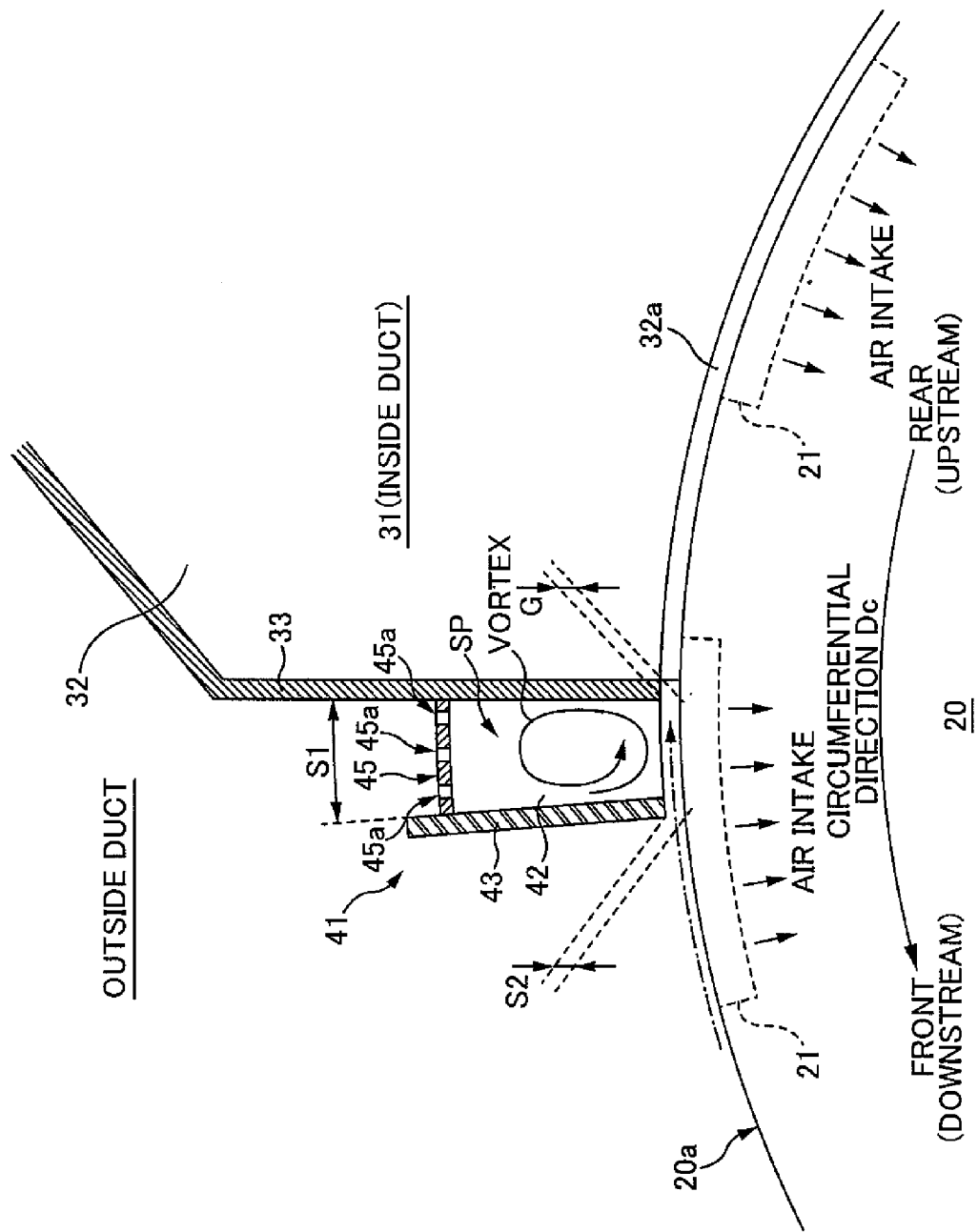
FIG. 4 is an explanatory diagram of a vortex that may be generated in the first chamber SP of the outside air intrusion inhibiting member 41.

FIG. 3A to FIG. 3C are explanatory diagrams of the outside air intrusion inhibiting member 41. FIG. 3A is a longitudinal sectional view thereof and FIG. 3B is a view seen along line B-B in FIG. 3A and FIG. 3C is a view seen along line C-C in FIG. 3A. For the purpose of a better view, FIG. 3A is shown by rotating FIG. 2 by 90 degrees in the anti-clockwise direction and in FIG. 3A and FIG. 3C, the contact seal 32a of the side wall 32 of the duct 31 is shown whereas the sheet shaped member 4 is not.

As shown in FIG. 3A and FIG. 3B, the outside air intrusion inhibiting member 41 is provided with a first front wall 43 disposed away from and opposing the front wall 33 of the duct 31 with a spacing S1 (corresponding to the first chamber SP) of 10 to 150 mm, a pair of right and left first side wall sections 42, 42 spanning between the first front wall section 43 and the front wall section 33 of the duct 31 to close the spacing S1 from both sides, and a first ceiling 45 opposing the outer circumferential surface 20a of the rotating drum 20 while spanning between the first front wall 43 and the front wall 33 of the duct 31. These walls 33, 42, 43 and 45 together define a chamber (hereinafter referred to as the first chamber SP) sectioned adjacent to and in communication with the gap G.

The first front wall 43 (corresponding to the first wall) is formed to have substantially the same width as the front wall 33 of the duct 31 and is disposed away from the outer circumferential surface 20a with a spacing S2 (corresponding to the second spacing) of 10 to 150 mm so to be in a non-contact state with the outer circumferential surface 20a of the rotating drum 20. In this way, outside air flows into the first chamber SP through gap S2 with the spacing S2 and as indicated by alternate long and short dashed lines in the figure, an outside airflow is formed along the outer circumferential surface 20a of the rotating drum 20 within this first chamber SP. This outside airflow reaches the gap G of the front wall 33 of the duct 31 and intrudes into the duct 31, in other words becomes an intruding outside air.

A plurality of penetration holes 45a are formed to the first ceiling 45. Hereby, as indicated by a chain double-dashed line in the figure, outside air straightened by these penetration holes 45a flows into this first chamber SP so that in this first chamber SP, outside airflow is made to flow along the direction substantially perpendicular to the outer circumferential surface 20a of the rotating drum 20 and this flow of outside air also reaches the gap G.

Shortly, the outside air that is to reach the gap G is divided into two flows one being a flow along the outer circumferential surface 20a indicated by alternate long and short dashed lines and the other being a flow along a direction substantially perpendicular to the outer circumferential surface 20a indicated by a chain double-dashed line. The latter is a flow in a direction substantially perpendicular to the outer circumferential surface 20a so that it is forced to turn to change its direction toward the gap G immediately before reaching the gap G, which leads to a dynamic pressure drop. Therefore, compared to the case where the first front wall 43 is not provided, it can be considered that energy of outside air decreases by an amount of at least the dynamic pressure lost and as a result intrusion of outside air through the gap G is restrained.

Another reason why the intrusion of outside air can be restrained is because the flow of outside air in a direction substantially perpendicular to the outer circumferential surface 20a (arrowed chain double-dashed line) is considered to interfere with the flow of outside air along the outer circumferential surface 20a (arrowed alternate long and short dashed line). In other words, in the vicinity of the gap G, the flow indicated by the former arrow of a chain double-dashed line confronts the flow indicated by the latter arrow of long and short dashed line coming from a substantially perpendicular direction thereof so that the flow of outside air indicated by the long and short dashed line interferes with the flow of outside air along the outer circumferential surface 20a. As shown in FIG. 3D, at this time it is assumed that a vortex is generated in the first chamber SP and here energy loss due to the generation of the vortex as well as restraint of outside air flowing in through the gap S2 due to the generated vortex are considered to contribute to restrain the intrusion of outside air into the duct 31.

To enhance the restraining effect of this intrusion of outside air, it is desirable that air suction is performed through the air intake holes at the bottom of the form die 21 at also the location of the first chamber SP so that the above mentioned outside flow (arrowed chain double-dashed line) created by an inflow from the penetration holes 45a is reliably formed. In this way it is conceived that, with this flow, the flow of outside air along the outer circumferential surface 20a of the rotating drum 20 (arrowed long and short dashed line) can be intercepted.

By the way, in order to effectively benefit from the restraining effect of the above mentioned intruding outside air, the gap S1 (spacing between the front wall 33 of the duct 31 and the first front wall 43) is preferably set to a value between 1 and 30 mm that is smaller than the above mentioned value between 1 and 50 mm and more preferably set between 3 and 10 mm.

It is desirable that the air pressure within the first chamber SP is set between the air pressure in the duct 31 and that outside the duct 31 by setting such as the number or diameter of the penetration holes 45a of the first ceiling 45. That is, a pressure value that exceeds the air pressure in the duct 31 and below that outside the duct 31 is favorable. In this way, this first chamber SP functions as a pressure moderating portion that restrains a sudden change of pressure between the high air pressure outside the duct 31 and low air pressure inside the duct 31. Therewith, the flow rate of outside air passing through the gap G can be reduced. In other words the path length between the space outside the duct 31 and that inside the duct 31 can be elongated, allowing to reduce the gradient of the pressure change (which is the amount of pressure change per unit length, referred herein also as "pressure gradient") between the low air pressure in the duct 31 and the high air pressure outside the duct 31. As a result, the flow rate of outside air flowing through the gap G can be reduced. Therewith, intrusion of outside air through gap G is further restrained. Further, since the flow rate of the outside air flowing along the outer circumferential surface 20a of the rotating drum 20 is reduced, peeling of pulp fiber from the absorbent body 1 being stacked in the form die 21 can be avoided allowing uniform stacking to be achieved.

Such penetration holes 45a are formed in, for example, perfect circles with a diameter of 2 to 6 mm. As their arrangement, in order to reduce regional unbalance of the pressure distribution in the first chamber SP, a pattern in which the penetration holes 45a are uniformly arranged in the front-rear direction and the side-to-side direction, respectively, of the first ceiling 45, as shown in FIG. 3B, is preferred and in this example a so-called hound's-tooth check arrangement is adopted. Particularly, rows of penetration holes configured with a plurality of penetration holes 45a are each aligned with a first spacing P1 in the right-left width direction and a second spacing P2 in the front-rear circumferential direction with each of the penetration hole rows adjacent in the circumferential direction displaced by half the pitch of the first spacing P1 (=P1/2) in the width direction.

Incidentally, in order to make the first chamber SP reliably function as the above described pressure moderating portion, the area ratio of the penetration holes 45a to the first ceiling 45 (including the area of the penetration holes 45a) is preferably set to any value between 10% and 80%. The reason for this is that if the ratio is under 10% it is substantially the same as the first ceiling 45 at a closed state where the air pressure in the first chamber SP would be substantially the same as that inside the duct 31. On the other hand, if it is over 80% it is substantially the same as an open state without the first ceiling 45 where the air pressure inside the first chamber SP would be substantially the same as that outside the duct 31. However, when the latter is beyond 80%, operational advantages (operation advantage of restraining the intrusion of outside air through the gap G with the above described dynamic pressure drop and the like by generating a flow of outside air along a direction substantially perpendicular to the outer circumferential surface 20a of the rotating drum 20), initially explained, can be effectively appreciated even if the first chamber SP does not function as a pressure moderating portion.

Second Embodiment

Figure 5:
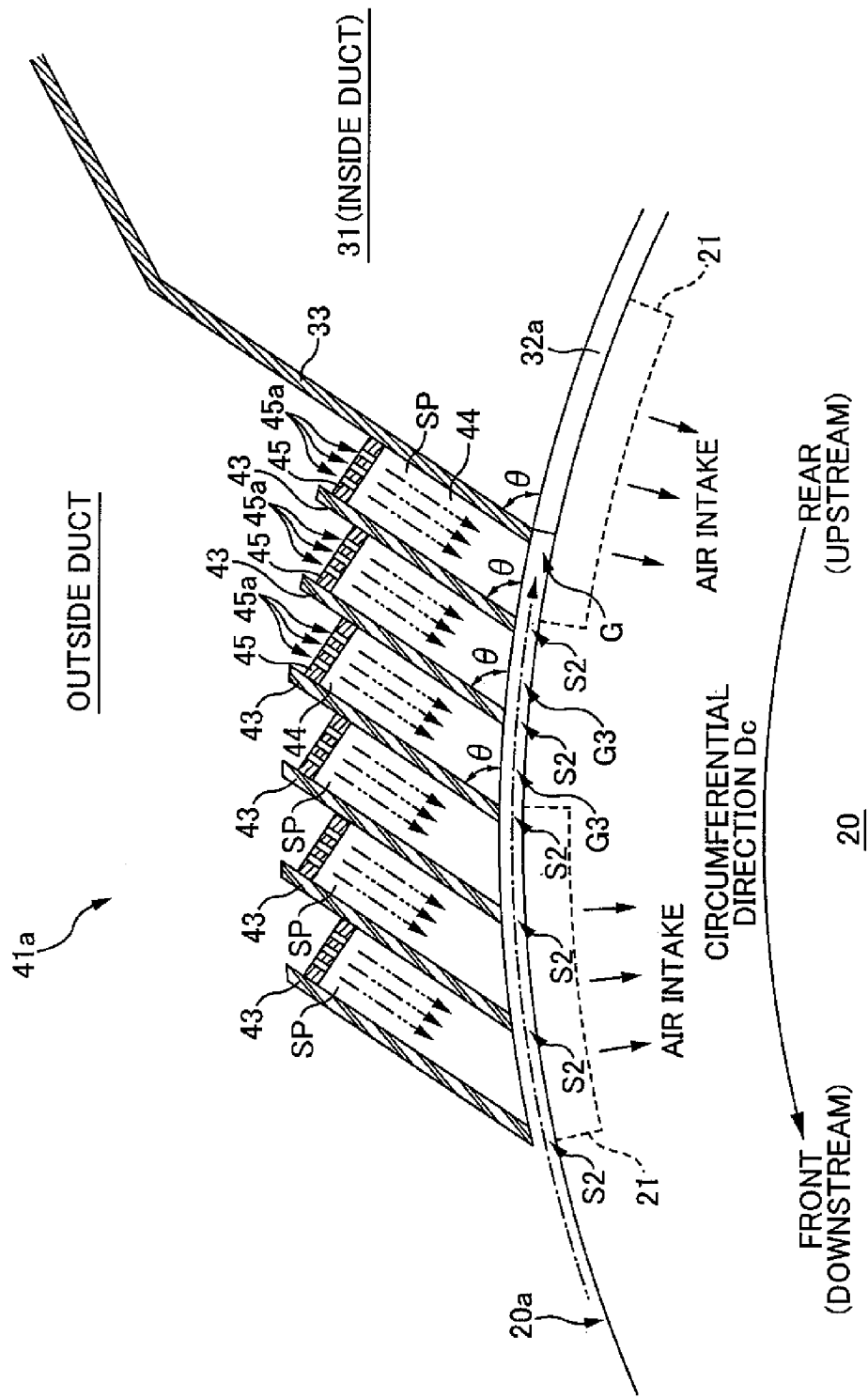
FIG. 5 is a longitudinal sectional view of the outside air intrusion inhibiting member 41a according to the second embodiment.

FIG. 5 is a longitudinal sectional view of an outside air intrusion inhibiting member 41a according to the second embodiment.

Here too, an explanation of the outside air intrusion inhibiting member 41a for the front wall 33 of the duct 31 is given as an example, but the same applies to the rear wall 34.

In the first embodiment, only a single chamber SP is partitioned adjacent the front of the front wall 33 of the duct 31, whereas the second embodiment mainly differs such as on the point that a plurality of chamber SPs are partitioned to align in the front-rear direction.

In other words, five similar chambers are partitioned to align on the downstream side of the first chamber SP along the outer circumferential surface 20a of the rotating drum 20. Each of the chamber SPs are specified in a manner similar to the above described first chamber SP, and is provided with a first front wall 43, a pair of right and left first side walls 42 and a first ceiling 45. And all the ceilings 45 also have a plurality of penetration holes 45a formed thereto.

However, the air pressure in each of the chamber SPs gradually changes, from an air pressure within the duct 31 to that outside the duct 31, along with the distance from the front wall 33 of the duct 31 toward the downstream side of the outer circumferential surface 20a of the rotating drum 20. Thereby, effect as a pressure moderating portion improves in proportion to the number of chambers increased and as a result, intrusion of outside air through the gap G can be furthermore effectively restrained.

Such adjustment of air pressure is, similar to the first chamber SP of the first embodiment, set by the area ratio of the penetration holes 45a to the first ceiling 45. That is, this ratio increases as the distance between the chamber SP and the duct 31 increases on the downstream side of the circumferential direction Dc.

Another difference is that in the first embodiment, as shown in FIG. 3A, each of the front wall 33 and the first front wall 43 of the duct 31 were positioned to extend in a direction substantially perpendicular (radius direction of the rotating drum 20) to the outer circumferential surface 20a of the rotating drum 20, whereas in the second embodiment, as shown in FIG. 5, the front wall 33 and the first front wall 43 of the duct 31 are positioned to incline toward the upstream side in the circumferential direction than the direction perpendicular to the outer circumferential surface 20a of the rotating drum 20 (radius direction of the rotating drum 20). That is, angle θ (the contained angle θ between the part where the front wall 33 faces the outer circumferential surface 20a of the rotating drum 20 and the front wall section 33, and the contained angle θ between the part where the first wall 43 faces the outer circumferential surface 20a of the rotating drum 20 and the first front wall section 43) shown in FIG. 5 is defined as an acute angle. In a case such an arrangement is adopted, the flow of outside air flowing in each chamber SPs through the penetration holes 45a of the first ceiling 45 (refer to the arrowed chain double-dashed lines), flows to counter, that is to knock out the flow of outside air flowing along the outer circumferential surface 20a (refer to the long and short dashed line) thereby allowing to effectively reduce the flow rate of the outside air flowing along the outer circumferential surface 20a. Additionally, the amount of dynamic pressure drop caused by the turning of the air flow indicated by chain double-dashed lines increases so that thereby, the intrusion of outside air through the gap G is effectively restrained. In order to improve this effect, the angle θ is preferably set to a value equal to or greater than 20° and smaller than 90°.

Incidentally, in order to generate an above described counter effect against the outside air intrusion inhibiting member 41a for the rear wall 34 of the duct 31, shown in FIG. 2, the rear wall 34 and the first front wall 43 should be positioned to incline toward the downstream side in the circumferential direction to exceed an angle that is perpendicular to the outer circumferential surface 20a of the rotating drum 20 (radius direction of the rotating drum 20).

Preferably, the spacing S2 between the outer circumferential surface 20a of the rotating drum 20 and the first front wall 43, shown in FIG. 5, is set to 0.3 to 1.8 times the spacing G between the outer circumferential surface 20a and the front wall 33 of the duct 31, and more preferably, it is set smaller than the gap G. Thereby, the flow of outside air at the first front wall 43 can be reliably inhibited, and as a result, the flow of outside air capable of flowing through the gap G of the front wall 33 of the duct 31 can be effectively restrained.

Other Embodiments

In the foregoing, embodiments of the present invention have been described. However, the present invention is not limited to these embodiments, and modifications such as those described below are possible.

In the foregoing embodiment, air 3 has been exemplified as an example of gas discharged form the duct 31, however, as long as it is gas that can be mixed with fluid absorbent fiber and does not cause chemical reaction or the like with the aforementioned fiber, the gas is not limited to such and nitrogen and the like can be used.

In the foregoing embodiment, an example was shown where the outside air intrusion inhibiting members 41a were provided to both the front wall 33 and the rear wall 34 of the duct 31, however, the outside air intrusion inhibiting member 41 can be provided to only either one of the two. But in such a case turbulent flow is likely to generate in the duct 31 compared to the case where both of the walls are provided with the outside air intrusion inhibiting members 41, 41, therefore it is preferable to provide the members to both walls.

In the foregoing embodiment, as shown in FIG. 3A, FIG. 3C and FIG. 5, a contact seal 32a is provided to each right and left side walls 32 configuring the duct 31, that is, the outside air intrusion inhibiting member 41 (41a) is not applied to the side walls 32, however the outside air intrusion inhibiting members 41 (41a) can be applied to these side walls 32. And if they are applied, the outside air intrusion inhibiting members (41) 41a do not contact the outer circumferential surface 20a of the rotating drum 20 so that component replacement due to wear by sliding can be omitted.

In the foregoing embodiment, a circular shape has been exemplified as a shape of the penetration holes 45a formed to the first ceiling 45 of the outside air intrusion inhibiting members (41) 41a however, the shape is not limited to such as long as the shape has an effect to straighten the flow and a polygonal shape or an ellipse, for example, can be used.

In the foregoing embodiment, a hound's-tooth check arrangement has been shown (see FIG. 3B) as an example of an arrangement of the penetration holes 45a of the first ceiling 45 however, the arrangement is not limited to such and the penetration holes 45, 45 adjacent to each other in the circumferential direction Dc can be aligned without their positions displaced in the width direction, for example.

In the foregoing embodiment, the first ceiling 45 was provided however, the first ceiling 45 can be omitted if the chamber SP need not function as a pressure moderating portion. In this case, the operational advantage that may be achieved with the outside air intrusion inhibiting member 41 (41a) is only "restraining the intrusion of outside air through the gap G by the above described dynamic pressure drop and the like caused by generating a flow of outside air flowing along the direction substantially perpendicular to the outer circumferential surface 20a of the rotating drum 20."

In the foregoing embodiment, presence or absence of a gap G3 between the outer circumferential surface 20a of the rotating drum 20 and the first side wall 42 of the outside air intrusion inhibiting member 41 (41a) was not mentioned however, from the viewpoint of restraining the intrusion of outside air into the duct 31, it is better not to have the gap G3 shown in FIG. 3A and FIG. 5. And in this case, an above mentioned brush shaped contact seal 32a, for example, is used. However, in a maintenance conscious case, the gap G3 should be in a state without a contact seal 32a.

In the foregoing embodiment, a configuration with form dies 21 formed on the outer circumferential surface 20a of the rotating drum 20 with the moving path of the form die 20 set in the circumferential direction Dc of the rotating drum 20 has been shown as an example however, as long as the form die 21 moves in one direction along a predetermined moving path, the configuration is not limited to the above. For example, a configuration can be adopted where the form dies 21 in recessed shapes are formed on the belt surface (corresponding to the predetermined surface) of a belt conveyor as the predetermined member and the belt is moved along a predetermined orbit with the duct 31 positioned at a predetermined position on the predetermined orbit.

In the foregoing embodiment, the size of the gap G between the distribution opening 31a of the duct 31 and the outer circumferential surface 20a of the rotating drum 20 was not mentioned (see FIG. 3A) however, this gap G can be set to any value within the range of 1 to 20 mm, for example.

In the above described embodiment, pulp fiber 2 (pulp pulverized into fibrous form) has been exemplified as fluid absorbent fiber however, cellulose such as cotton, regenerated cellulose such as rayon and fibrillated rayon, semi-synthetic cellulose such as acetate and triacetate, fibrous polymers, and thermoplastic fibers may also be used, or these fibers may also be used in combination.

LIST OF REFERENCE NUMERALS 1 absorbent body, 2 pulp fiber (fluid absorbent fiber), 3 mixed air (gas), 4 sheet shaped member
10 fiber stacking apparatus (absorbent body manufacturing apparatus), 10a fiber stacking apparatus,
20 rotating drum (specific member), 20a outer circumferential surface (specific surface),
21 form die, 25 roller,
31 duct,
31a distribution opening (opening), 31b upper end opening,
32 side wall, 32a contact seal,
33 front wall (wall of duct, wall located on the downstream side within the moving path),
34 rear wall (wall of duct, wall located on the upstream side within the moving path),
38 charge duct,
41 outside air intrusion inhibiting member, 41a outside air intrusion inhibiting member,
42 first side wall (side wall), 43 first front wall (first wall),
45 first ceiling (ceiling),
45a penetration hole,
G gap, G3 gap
S1 spacing (first spacing), S2 spacing (second spacing),
SP first chamber, SP chamber, Ps supply position, Pf demolding position

The invention claimed is:

1. An apparatus for manufacturing an absorbent body, comprising:
    a form die that is formed in a recessed shape on a predetermined surface of a predetermined member and that moves in one direction along a moving path along the predetermined surface; and
    a duct that is positioned at a predetermined position on the moving path and that discharges gas containing fluid absorbent fiber from an opening toward the predetermined surface;
    wherein an absorbent body is formed by suction of the gas through an intake hole at a bottom of the form die to stack into the form die fluid absorbent fiber contained in the gas when the form die passes by the position of the duct,
    the apparatus further having
    a gap formed between the predetermined surface and an opening of the duct,
    a gas pressure inside the duct that is lower than a gas pressure outside the duct by suction of the gas from the bottom of the form die,
    a first wall outside the duct, the first wall spaced from a wall of the duct by a first spacing and spaced from the predetermined surface by a second spacing, and
    an outside gas flow along a direction intersecting with the predetermined surface and an outside gas flow along the predetermined surface made to reach the gap by the first wall.

2. An apparatus for manufacturing an absorbent body according to claim 1,
    wherein the first wall is provided to at least either a wall of the duct located at an upstream side of the moving path or a wall of the duct located at a downstream side of the moving path.

3. An apparatus for manufacturing an absorbent body according to claim 2,
wherein a pair of side walls are provided, the side walls extending between the wall of the duct and the first wall to close the first spacing from the sides.

4. An apparatus for manufacturing an absorbent body according to claim 2,
wherein a first chamber is partitioned adjacent to the gap with the first wall and the wall of the duct, the first chamber being in communication with the inside of the duct via the gap,
and gas pressure inside the first chamber is set lower than a gas pressure outside the duct and higher than a gas pressure inside the duct.

5. An apparatus for manufacturing an absorbent body according claim 4,
wherein at least one or more opposing walls are spaced from an adjacent wall, including the first wall, in a direction along the moving path at positions, along the moving path, that are farther away from the wall of the duct than the first wall, the walls being spaced from the predetermined surface,
gas pressure inside each of the chambers partitioned by adjacent walls along the moving path becomes closer to a gas pressure outside the duct as each of the chambers, including the first chamber, are farther away from the wall of the duct.

6. An apparatus for manufacturing an absorbent body according to claim 5,
wherein each of the chambers have a pair of side walls that extend between the adjacent walls in the direction along the moving path to close the sides of the chamber, and a ceiling that extend between the adjacent walls in the direction along the moving path and that is positioned to oppose the predetermined surface, and
the ceiling has a plurality of penetration holes formed thereto.

7. An apparatus for manufacturing an absorbent body according to claim 6,
wherein a ratio of an area of the plurality of penetration holes to an area of the ceiling becomes larger as a chamber of the plurality of chambers, including the first chamber, is farther away from the wall of the duct.

8. An apparatus for manufacturing an absorbent body according to claim 2,
wherein a size of a spacing between the walls, except the wall of the duct, and the predetermined surface is smaller than a spacing between the wall of the duct and the predetermined surface and larger than zero.

9. An apparatus for manufacturing an absorbent body according to claim 2,
wherein a suction of gas from the bottom of the form die is also performed at the first spacing between the first wall and the wall of the duct.

10. An apparatus for manufacturing an absorbent body according to claim 1,
wherein the predetermined member is a rotating drum that continuously rotates in one direction along a circumferential direction,
the form die is formed in a recessed shape on an outer circumferential surface, as the predetermined surface, of the rotating drum, and the form die is moved along the path in the circumferential direction as the moving path along with a rotation of the rotating drum in the circumferential direction, and
the opening of the duct is provided to oppose the outer circumferential surface of the rotating drum at a predetermined location in the circumferential direction.

11. A method for manufacturing an absorbent body, comprising:
using a recessed form die formed on a predetermined face of a predetermined member, moving in one direction along a moving path along the predetermined face;
using a duct disposed in a predetermined position in the moving path, discharging a gas including fluid absorbent fibers from an opening section toward the predetermined face;
forming an absorbent body by suction of the gas through intake holes at a bottom section of the form die to stack into the form die the fluid absorbent fibers included in the gas when the form die passes by the position of the duct;
wherein a gap is formed between the predetermined face and the opening section of the duct,
a gas pressure inside the duct is lower than a gas pressure outside the duct by suction of the gas from the bottom section of the form die,
a first wall, outside the duct, is spaced from a wall of the duct by a first spacing and spaced from the predetermined face by a second spacing, and
an outside gas flow along a direction intersecting with the predetermined face and an outside gas flow along the predetermined face are made to reach the gap by the first wall.

* * * * *